(12) United States Patent
Whiteside

(10) Patent No.: US 6,475,220 B1
(45) Date of Patent: Nov. 5, 2002

(54) SPINAL CABLE SYSTEM

(75) Inventor: Leo A. Whiteside, St. Louis County, MO (US)

(73) Assignee: Whiteside Biomechanics, Inc., St. Louis, MO (US)

( * ) Notice: Subject to any disclaimer, the term of this patent is extended or adjusted under 35 U.S.C. 154(b) by 0 days.

(21) Appl. No.: 09/568,736

(22) Filed: May 11, 2000

Related U.S. Application Data

(60) Provisional application No. 60/159,750, filed on Oct. 15, 1999.

(51) Int. Cl.$^7$ ............................................. A61B 17/82
(52) U.S. Cl. ........................... 606/74; 606/72; 606/224
(58) Field of Search ............................ 606/60, 61, 72, 606/74, 224, 222; 24/28, 29, 131 R

(56) References Cited

U.S. PATENT DOCUMENTS

| | | | | |
|---|---|---|---|---|
| 5,318,566 A | * | 6/1994 | Miller | 606/60 |
| 5,725,582 A | * | 3/1998 | Bevan et al. | 623/17 |
| 5,908,421 A | * | 6/1999 | Beger | 606/61 |
| 5,997,542 A | * | 12/1999 | Burke | 606/74 |
| 6,264,675 B1 | * | 7/2001 | Brotz | 606/228 |
| 6,387,099 B1 | * | 5/2002 | Lange et al. | 606/74 |

* cited by examiner

*Primary Examiner*—Nicholas D. Lucchesi
*Assistant Examiner*—Michael B. Priddy
(74) *Attorney, Agent, or Firm*—Polster, Lieder, Woodruff & Lucchesi, L.C.

(57) ABSTRACT

A surgical cable system is provided which includes a surgical cable and a passer for passing the cable around a bone to which the cable is to be secured. The cable includes a main cable having a lead cable attached to one end of the main cable and a fastener preattached to the first end of the main cable. The lead cable has an enlargement (a bead) affixed to its free end. The passer includes a curved probe and a recess or cavity is provided in the probe near its tip and a slot extends from the cavity to the tip of the probe. The cavity is sized to accept the enlargement of the lead cable and the slot is sized to receive the lead cable so that as the probe is withdrawn (pulled) from under the bone, the lead cable and the main cable are pulled under the bone so as to minimize the space required to pass the cable. The lead cable and a portion of the main cable may then be inserted in the fastener. The cable is then tensioned to a desired level and the fastener is crimped so as to secure the cable around the bone with the desired level of tension.

20 Claims, 1 Drawing Sheet

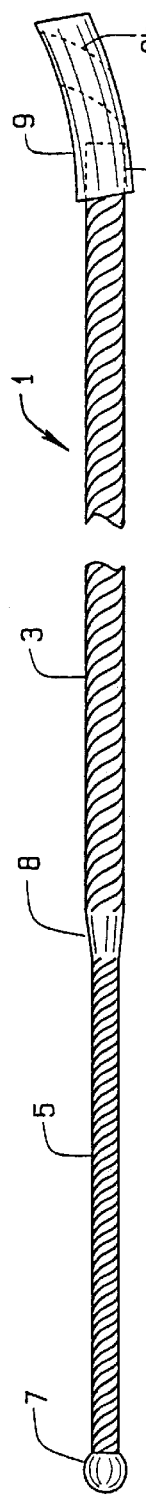
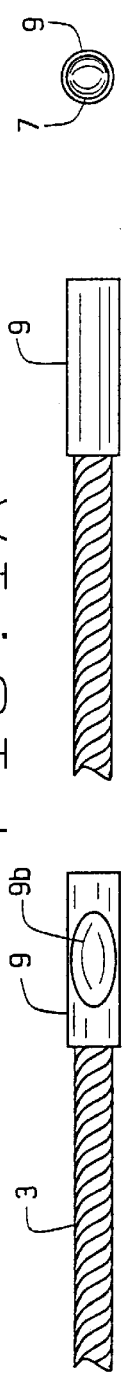
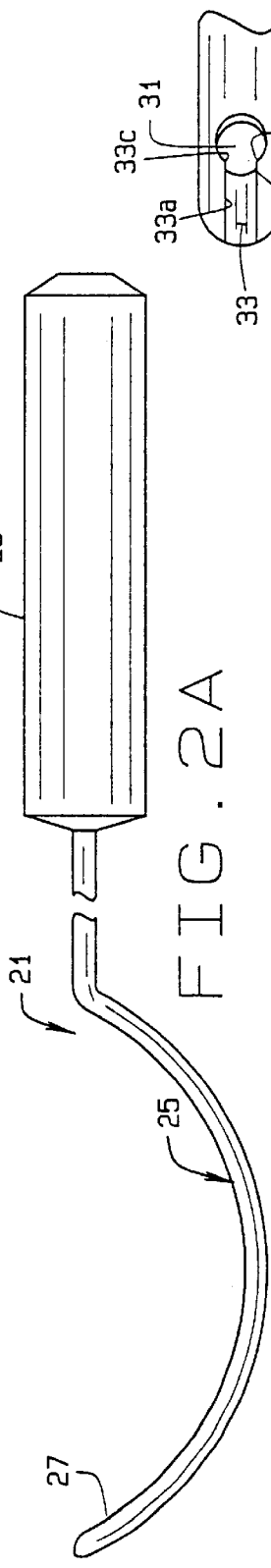
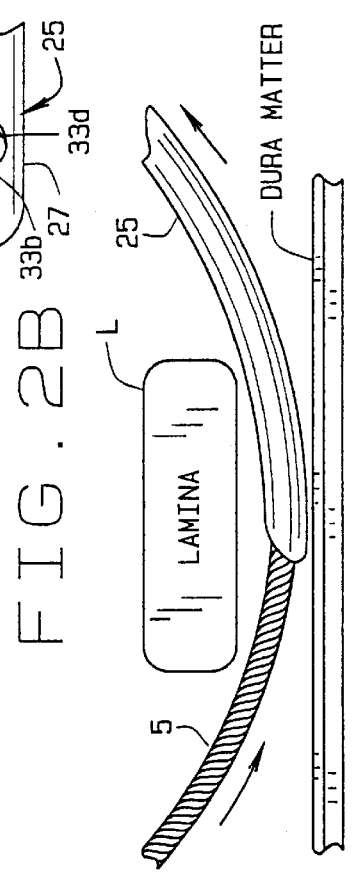
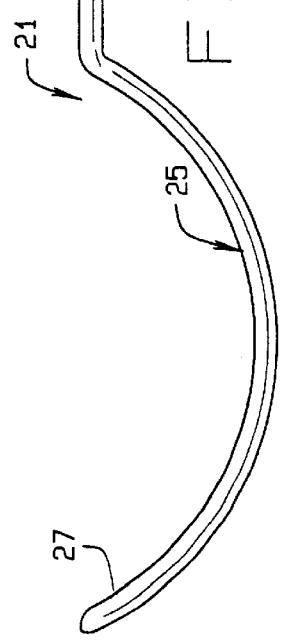
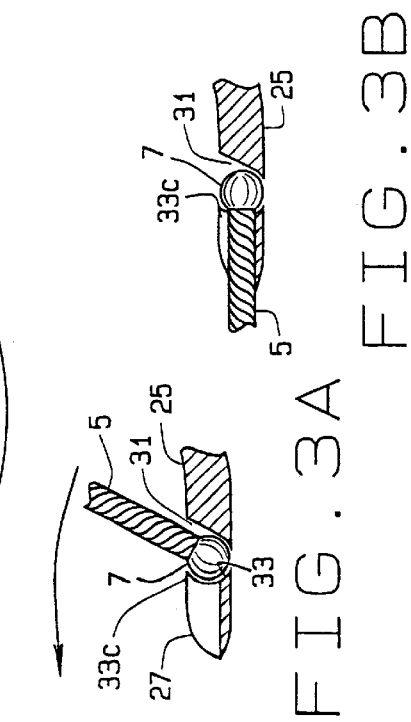

SPINAL CABLE SYSTEM

CROSS-REFERENCE TO RELATED APPLICATIONS

In accordance with 35 USC §119(e), this application claims priority based on U.S. Provisional Application No. 60/159,750, filed Oct. 15, 1999.

STATEMENT REGARDING FEDERALLY SPONSORED RESEARCH OR DEVELOPMENT

Not Applicable.

BACKGROUND OF THE INVENTION

This invention relates spinal cables, and, in particular, a new and improved system including a spinal cable and passer for positioning the spinal cable adjacent a patient's spine.

Wires and flexible cables have been used for some time to secure fixation devices in the spine when fractures are repaired surgically, and when the spine is straightened or fused. These wires are passed under the lamina of the posterior elements of the vertebra, and then wrapped around a metal rod, or around an adjacent bone structure such as another lamina or a bone graft strut. When tightened, these cables hold the vertebrae rigidly to the fixation device or to each other, and apply forces used to correct deformity or provide rigid fixation to allow healing of fractures and fusions. Other bones are often repaired in the same manner; using cables passed around the bone. In most circumstances the anatomical structures behind the bone are subject to damage if the cable is accidentally passed into the surrounding soft tissue, or if the passer accidentally excoriates or compresses these structures as the cable is passed.

In some areas of the spine, and in certain conditions, the space between the undersurface of the lamina and the dura and spinal cord is very small. Thus, care must be taken so that these structures are not compressed and damaged by the instrument used to pass the cable and by the cable itself during the process of passing it under the lamina. For this reason flexible, multi-wire strand cables are usually preferable to relatively rigid monofilament (or solid) wires. However, passing a flexible cable between the lamina and the dura can be difficult. Heretofore, relatively stiff monofilament lead wires have been attached to the cable ends to facilitate passage of the flexible cable between the lamina and dura. These monofilament wires, however, are not sufficiently stiff to create a reliable pathway between the dura and the undersurface of the lamina, and may fail to pass or else create a false passage into the dura and spinal cord. Moreover, these monofilament lead wires required that the lead wire and the cable be pushed as they were passed under the bone. While these lead wires were stiff, they nevertheless were subject to bending as they were pushed under the bone. If the lead wire or the cable attached thereto would bend during inserting, such bent areas or deformities in the rigid lead wire could compress or damage the dura and/or the spinal cord as they are pushed through the space between the lamina and underlying structures.

In some cases a separate instrument is used to pass the cable or wire between the lamina and dura. These passers are generally tubular structures through which the cable or wire is passed, and therefore are considerably thicker that the cable or wire itself. Use of these prior passers therefore may endanger the spinal cord and dura. One such device is disclosed by U.S. Pat. No. 4,557,259 to Wu in which a series of instruments is described to probe and progressively enlarge the space between the lamina and underlying neural structures and finally allow passage of a tubular device which then allows a wire to be inserted under the lamina. Then the tubular passer is removed.

These problems and restrictions occur, to a varying degree, in all surgical procedures that repair bone with cables passed around the bone structure. Similar conditions exist in cardiovascular surgery during repair of the sternum, and devices have been developed to ensure passage of the fixation band without damage to underlying structures. One such device incorporates a needle attached to a flexible length of suture, which, in turn, is attached to a stiffer and stronger band which itself has a fastener attached to the opposite end. An example of such a device is shown in U.S. Pat. No. 5,089,012 to Prou. The surgical suture disclosed in Prou is stated to be used in open heart surgery for sternotomy closure. This device is unacceptable for use in the spine and around long bones because the plastic strap is too large and bulky to pass safely next to the dura and spinal cord. Also, a needle that is preattached to the device is inconvenient because it will not pass through a conventional cable tensioning device, but instead must be cut off, leaving a loose end (i.e., the wire strands comprising the cable are loose and can begin to unravel) that is difficult to handle.

Passing the flexible cable with a passer that is pushed around the bone or under the lamina is one possible means to solve the problem of passing the cable safely. However, the cable must have a thickness of at least 1.5 mm to achieve adequate strength for general use in the spine and other bone structures. This thickness of cable is often too stiff to grasp and pull under the lamina or around the bone without using an instrument that is too bulky to pass safely in areas with limited space. Such a passer that is pushed under a bone and carries the cable with it is shown in my co-assigned U.S. Pat. No. 5,772,663.

There is a need for a strong and flexible cable that is easy to pass under the lamina or around the bone even in constricted areas, and for a thin passer device that can be passed under the lamina or around the bone with careful surgical control and can pull the cable through without endangering the underlying dura and spinal cord or other structures. The cable must be flexible enough to bend easily without kinking and without compressing the underlying soft tissue structures, but must also be strong and thick enough to function adequately for stabilization of the spine. The passer must be sufficiently rigid to allow firm control while it is being passed under the lamina, but must be sufficiently thin so as to avoid compressing the fragile structures on the other side. The grasping mechanism must also be thin and smooth, and the cable adjacent to the grasping mechanism must not be kinked, so that passing the cable tip does not tear or compress the dura and spinal cord.

BRIEF SUMMARY OF THE INVENTION

Among the objects and features of this invention may be noted the provision of an orthopedic cabling system having a main cable and a flexible lead cable which may be pulled behind (under) a bone with minimal damage or trauma to the tissue or structure behind or under the bone;

The provision of such a cabling system in which the fastener is preattached to the main cable so as to eliminate the need for the surgeon having to handle loose fasteners;

The provision of such a cabling system in which includes a passer which the surgeon may use to pass the cable around or under the bone;

The provision of such a cabling system in which the passer is of a minimal diameter or cross section and yet has sufficient strength and stiffness to enable the passing of the cable around the bone;

The provision of such a cabling system in which the passer is first inserted behind the bone without the cable attached to the passer and, when the end of the passer is accessible to the surgeon on the other side of the bone, permits the cable to attached to the passer and to be pulled under the bone outside of the passer as the surgeon withdraws the passer; and The provision of such a cabling system which is of economical construction, which is easy for a surgeon to use, which requires little specialized training for a surgeon to use, which securely fastens the cable around the bone while maintaining a desired level of tension in the cable.

Other objects and features of this invention will be in part pointed out and in part described hereinafter.

Briefly stated, a surgical cable and passer system of the present invention comprises a cable assembly including a flexible main cable having a first end and a second end, a thinner and more flexible lead cable attached to one end of the main cable, with the lead cable having a bead affixed to one end of the lead cable. A fastener is preattached to the end of the main cable opposite the lead cable. The cabling system includes a passer having an elongate probe having a thickness less than about three (3) times, and more preferably less than about 2½ times, the diameter of the main cable. The passer probe has a recess therein proximate its distal end and a slot within the passer probe extends from the recess to the free end of the probe. The passer probe is insertable under the bone without the cable so that the free end of the passer is visible on the side of the bone opposite to that from which it was inserted. With the free end of the passer probe accessible on the other side of the bone, the bead on the lead cable is inserted into the recess in the end of the probe and a portion of the lead cable proximate the bead is received within the slot such that at least a portion of the lead cable extends endwise from the probe. With the lead cable so coupled to the passer probe, the surgeon may withdraw the passer probe from under the bone thus pulling the lead cable and the main cable behind the probe. In this manner, the lead cable and the main cable are passed beneath the bone in such manner as to minimize the space required. The fastener preattached to the main cable has a bore therethrough for receiving the free end of the lead cable with the bead thereon and at least a portion of the main cable. The fastener is deformable so as to permanently secure the main cable within the bore while maintaining the desired level of tension on the main cable banded about the bone. A method of passing a cable and permanently banding the cable about the bone with a desired level of tension in the cable is also disclosed.

BRIEF DESCRIPTION OF THE SEVERAL VIEWS OF THE DRAWINGS

FIG. 1A is a side view of the cable with bead, lead cable, main cable and fastener;

FIG. 1B is a top plan view of the fastener at the end of the cable;

FIG. 1C is a bottom plan view of the fastener at the end of the cable;

FIG. 1D is a front elevational view of the bead at the front of the cable;

FIG. 2A is a side elevational view of the passer;

FIG. 2B is a top plan view of the tip of the passer;

FIG. 3A is a cross-section view of the tip of the passer with the cable bead being positioned in the passer's central depression;

FIG. 3B is a cross-sectional view of the tip of the passer with the cable bead in positioned in the passer's central depression to be pulled under the lamina;

FIG. 4 is a cross-sectional view of the lamina, the sublaminal space, the dura, and the spinal cord with the cable engaged in the passer.

Corresponding reference numerals indicate corresponding parts throughout the several view of the drawings.

DETAILED DESCRIPTION OF THE INVENTION

The following detailed description illustrates the invention by way of example and not by way of limitation. This description will clearly enable one skilled in the art to make and use the invention, and describes what I presently believe is the best mode of carrying out the invention.

The cable component in the present invention includes a flexible cable 1 for spine surgery including fusion and correction of deformity. However, it will be understood that the cable and passer of the present invention have uses in orthopedic surgery other than in spine surgery. The cable 1 (FIGS. 1A–1D) includes a flexible main cable 3, a lead cable 5 attached to one end of the main cable 3, and an enlarged bead 7 secured to the free end of the lead cable 5. The lead and the main cables are in line with one another. The lead cable 5 is preferably butt welded to the main cable 3, but those skilled in the art will realize that the lead cable may be secured to the end of the main cable in a number of ways, such as soldering or even with a crimp-type mechanical fastener. Preferably, the junction between the lead and main cables is a smooth junction or transition, as indicated at 8, such that there is no sharp step, but rather a sloped transition, between the lead and main cables. Where the lead cable is butt welded to the main cable, the transition may be silver soldered so as to provide this smooth transition, as indicated at 8 in FIG. 1A.

Main cable 3 is shown to be a multi-strand or multi-wire cable having a generally cylindrical cross section, preferably having a diameter of about 1.5 mm. (about 0.59"). The lead cable 5 is also of multi-strand construction and preferably has a diameter of approximately 0.75 mm (0.29") diameter, about half the diameter of the main cable. Further, bead 7 preferably has a diameter of approximately 1.5 mm (0.59"). As noted, the diameter of bead 7 which is approximately equal to the diameter of the main cable 3, however, within the broader aspects of this invention the diameter of the bead may be of any suitable diameter within the context of this invention. Because the lead cable 5 is of a smaller diameter than main cable 3, the lead cable is considerably more flexible than the main cable 3. A fastener, preferably a crimp-type fastener, as indicated at 9, is preattached (swaged) to the free end of the main cable 3. This fastener 9 is shown to be a short length of tubular titanium alloy having a cable attachment bore 9a and a cable crimping bore 9b inclined with respect to the axis of the tube. At the factory, the fastener is preferably preattached to the main cable 3 by inserting one end of the main cable into the attachment bore 9a and by swaging the fastener in the region of bore 9a so as to deform the tube into permanent gripping relation with the end of the cable received within bore 9a. In this manner, fastener 9 is preattached to the cable. It will be understood that when it is said that the fastener is in permanent gripping relation with the cable, it means that the fastener cannot be removed or loosened unless the fastener is damaged or destroyed. It will be further understood that within the broader aspects of this invention, fasteners other than crimp-type fasteners may be used. For example, a mechanically actuable cable fastener, such as is shown in FIGS. 1–4 in U.S. Pat. No. 5,702,399 to Kilpela et al. may be used.

Preferably, the fastener is slightly curved to accommodate the curvature of the bone or fixation device. Bore 9b is of sufficient diameter as to allow the bead 7 on the free end of the lead cable 5 and the main cable to pass through bore 9b. For example, where the diameter of bead 9 and main cable 3 is approximately 1.5 mm., the diameter of bore 9b is somewhat greater than 1.5 mm. so that the bead and the main cable may be readily passed through bore 9b by the surgeon.

While cables 3 and 5, bead 7, and fastener 9 may be made of a variety of metal alloys suitable for surgical use, one alloy that may be preferred is a titanium alloy made in accordance with the material specifications of ASTM F136-96. Preferably, the main cable is of a 7×7×0.00064 inch wire construct. That is, main cable is made of 7 bundles of twisted wires with each bundle having 7 wires with each wire having a diameter of 0.00064 inches. The lead cable is also of a multi-strand construction. Preferably, fastener 9 is made of the same or similar titanium alloy as the cables. The tube may be annealed to nearly a dead soft heat treat so that it may be crimped both to swage the fastener to the end of the main cable and to allow the fastener to be crimped to the cable by the surgeon thereby to permanently grip the main cable while maintaining a desired level of tension of the cable. Further, such a heat treat will lessen the tendency of the fastener to split as it is crimped.

In accordance with this invention, a passer 21, as shown in FIGS. 2A–2B is used to pull (rather than push) the cable under the lamina. Passer 21 is a curved blunt surgical probe made of surgical stainless steel or other suitable material, as would be well known to those skilled in the design of surgical instruments. On one end of the passer has a handle 23 which allows the probe end 25 to be conveniently manipulated by the surgeon in areas around the spine. The probe end 25 is curved with a radius of approximately 4 cm. (1.6 in.) and has a generally flat profile, with a thickness of about 3 mm. (0.118 in.). It will be particularly noted that the thickness of probe 25 is about twice the diameter of main cable 3. In accordance with this invention, it is preferred that the thickness of passer probe 25 be less than about three (3) times the thickness of the main cable, and preferably thinner, for example less than about 2½ times the thickness of the main cable. In this manner, the void formed in the tissue upon the insertion of the probe under the bone is minimized.

Probe 25 has a tapered tip 27, as is shown in FIG. 3A, but is still sufficiently blunt and smooth to allow dissection between the periosteum of the lamina and the dura covering the spinal cord. Tip 27 has a cavity or recess 31 that receives bead 7 on the end of lead cable 5. The tip of the passer has a slot or channel 33 therein for receiving a portion of the lead cable proximate the bead so as to allow the end of the lead cable to be coupled to the passer in such manner as to permit the surgeon to pull the cable under the lamina (or other bone) as the surgeon withdraws the passer. Cavity or recess 31 is preferably part spherical in shape and is sized to as to receive bead 7 and so to hold the bead captive within the cavity. Cavity 31 is preferably located about 3 mm. (0.118 in.) from the tip of the probe end of the passer. Channel 33 has spaced sidewall 33a, 33b (see FIG. 2B) and the inner ends of these sidewalls form a part of recess 31 and engage the sides of bead 7 when the latter is received in the recess so as to prevent the bead from being drawn through the channel 33. As best shown in FIGS. 3A and 3B, the inner ends 33c, 33d of channel 33 are part spherical in shape so as to engage one side of the spherical bead 33 so as to aid in preventing the bead from becoming disengaged from cavity 31.

In use, the surgeon passes (pushes) the passer probe end 25 under or behind the bone such that the tip 27 is accessible on the other side of the bone. The surgeon inserts the bead 7 on the free end of lead cable 5 into cavity 31 in the tip of the passer probe (as shown in FIG. 3A) and then rotates the cable downwardly (as shown by the arrow in FIG. 3A) such that the portion of the lead cable proximate the bead is received within slot or channel 33, as shown in FIG. 3B. The ends 33c, 33d of slot 33 help to retain the bead 7 within cavity 31. With the bead 7 and lead cable 5 so installed within the tip of the passer, the surgeon is thus able to pull or to withdraw passer probe 25 in the reverse direction (as shown by the arrows in FIG. 4) from which it was passed under the bone without the cable installed. As the passer probe 25 is withdrawn from under the bone, lead cable 5 extends from the tip of the passer and is generally in line with the axis of the passer probe. Thus, as the passer is withdrawn, the lead cable along with main cable 5 is pulled under the bone. As can be seen in FIG. 4A, the space required to pass cable 1 under the bone is only the diameter of the passer probe 25. This minimizes the space required and effectively eliminates kinks or bends from forming in the cable as it is passed under the bone.

FIG. 3A is a cross section through the tip 27 of the probe portion of the passer. The bead 7 is positioned in the part-spherical cavity 31. The roughly spherical cavity 31 overhangs the bead 7, so that the bead is substantially captured in the spherical cavity when the passer is pulled under the lamina. FIG. 3B shows the passer 21 with the bead 7 captured in the cavity 31 under the inner channel ends 33c, 33d when the bead is received in the cavity, the lead cable is received within slot or channel 33 and which the bead is drawn into contact with the channel ends 33c, 33d. Because the lead cable is pulled by probe 25, the lead cable automatically assumes a position generally parallel to the axis of the passer probe 25 when the cable is drawn under the lamina with the passer, and this occurs without bending the cable at a sharp angle or causing downward pressure that could push the passer into the dura and spinal cord. FIG. 4 shows the passer probe 25 under the lamina L with the bead (not visible in FIG. 4) captured in the spherical cavity and the lead wire in the slot. The pulling action of the probe 25 and surrounding tissue or bone (e.g., the lamina L, as shown in FIG. 4) holds the lead cable in the passer until the cable has been passed under the lamina and until the tip of the probe is moved clear of the tissue. Once the cable is passed under the lamina and is clear of tissue, lead cable 5 may be easily disengaged from passer 21 by the surgeon. The surgeon may then manually pull any additional length of the lead cable 5 and the main cable 3 under the bone, as required. Bead 7 and the lead cable 5 are then passed through the bore 9b of the fastener 9 and pulled taut. As is known, a tensioner can be used to achieve the proper tension in the cable 1. The fastener 9 is then crimped to secure the cable at the desired tension and cut. My co-assigned U.S. Pat. No. 5,772,663 discloses a screw type cable tensioner and a crimping tool that may be used in conjunction with the present invention and this U.S. Pat. No. 5,772,663 is hereby incorporated by reference.

It will be understood that an important attribute of the present invention is that the cross section of passer probe 25 is only slightly larger than the diameter of the bead 7 and of the main cable 3. Preferably, the diameter of the probe is less than about three (3) times the diameter of the main cable, and even more preferably, less than about 2½ time or less than the thickness of the main cable. This relative thin cross section of the probe (while maintaining adequate stiffness to enable the surgeon to push the probe behind the bone) is enabled because the probe need not carry or house the cable as the probe is pushed behind the bone. Instead, the passer of this invention allows the lead cable to be attached to the end of the probe after the surgeon has inserted the probe behind the bone and then the cable is pulled behind (not within) the probe as the latter is withdrawn from behind the bone. By enabling the probe to be of such a minimal diameter, the trauma caused to underlying tissue or structure is minimized.

In this disclosure, the terms "under the bone" and "beneath the bone" were used to describe how the cable of this invention was installed to allow the surgeon to band the cable around the bone. It will be understood that these terms should not be interpreted in a limiting sense and do not mean that the cable is only to be passed under the bone in a vertical sense, but it is a term of art to mean that the cable is passed behind a bone or other structure regardless of the vertical orientation of the bone.

Further, while the bead 7 illustrated and described herein is shown to be a spherical member, it will be understood that beads of other shapes may be used.

As various changes could be made in the above constructions without departing from the scope of the invention, it is intended that all matter contained in the above description or shown in the accompanying drawings shall be interpreted as illustrative and not in a limiting sense.

What is claimed is:

1. A surgical cable assembly comprising: a flexible main cable having a first end and a second end; a flexible lead cable attached to said main cable first end, said lead cable having a first end, a free end and an enlargement on its free end; the flexible lead cable being integrally attached to the main cable as to blend with the main body of the cable and wherein the enlargement is an integrally-attached solid bead attached to the lead cable, said bead having a cross section larger than the cross section of said lead cable and approximately the cross section of the main cable.

2. The surgical cable assembly of claim 1 further comprising a passer having an elongate probe having a thickness no greater than about 3 times the diameter of said main cable.

3. The surgical cable assembly of claim 2 wherein said probe has a distal end, said distal end having a tip and a recess near said tip, a slot within said tip extending from said recess to the distal end of the probe, said probe being insertable under a bone without the cable, said recess receiving said bead on said lead cable, said slot receiving a portion of said lead cable proximate said bead such that the remaining portion of said lead cable extends endwise from the tip of the probe, such that upon the probe being withdrawn from under the bone said lead cable and said main cable are pulled behind the probe and passed beneath the bone.

4. A surgical cable and passer system comprising a cable assembly comprising: a flexible main cable having a first end and a second end, a thinner and more flexible lead cable attached to one end of said main cable, said lead cable having a free end, a bead affixed on said lead cable proximate its free end, a fastener preattached to the end of said main cable opposite said lead cable, and a passer having an elongate probe having a thickness less than about three times the diameter of said main cable, said passer probe having a free end and a recess in said probe proximate its distal end, a slot within said passer extending from said recess to the free end of the probe, said passer probe being insertable under a bone without the cable, said recess receiving said bead on said lead cable, a portion of said lead cable proximate said bead being received within said slot such that at least a portion of said lead cable extends endwise from the probe, such that upon a surgeon withdrawing the passer probe from under the bone said lead cable and said main cable are pulled behind the probe thereby to pass the lead cable and the main cable beneath the bone, said fastener having a bore therethrough for receiving the free end of said lead cable with said bead thereon and at least a portion of said main cable, said fastener being deformable so as to permanently secure said main cable within said bore thereby to band the main cable about the bone.

5. A surgical cable and passer system comprising a flexible cable having a bead affixed to one end thereof and a fastener preattached to the other end thereof, and a passer having an elongate probe having a thickness less than about three times the diameter of said cable, said probe having a distal end and a recess in said probe proximate its distal end, a slot within said passer extending from said recess to the distal end of the probe, said probe being insertable under a bone without the cable, said recess receiving said bead on said cable, a portion of said cable proximate said bead being received within said slot such that at least a portion of said cable extends endwise from the probe, such that upon a surgeon withdrawing the probe from under the bone said cable is pulled behind the probe thereby to pass the cable beneath the bone, said fastener having a bore therethrough for receiving the distal end of said cable with said bead thereon and at least a portion of said cable, said fastener being actuable so as to secure said cable within said bore thereby to band the cable about the bone.

6. A surgical cable and passer system as set forth in either claim 4 or claim 5 wherein the thickness of the passer is preferably less than about 2½ times the diameter of said main cable.

7. A surgical cable and passer system as set forth in claim 5 wherein said cable includes a main cable and a lead cable, said lead cable being of a smaller diameter than said main cable and being more flexible than said main cable, one end of said lead cable being affixed to one end of said main cable, and the other end of said lead cable having said bead secured thereto, said main cable having said fastener preattached to its other end.

8. The surgical cable system of claim 7 wherein the fastener is pre-attached to said free end of the main cable.

9. The surgical cable system of claim 7 wherein said bead is affixed to said lead cable and has a diameter approximately equal to the diameter of the main cable.

10. The surgical cable system of claim 7 wherein said bead is generally spherical, and wherein said recess in said passer probe is generally part-spherical and sized to at least in part receive said bead to hold the lead cable relative to the probe.

11. The surgical cable system of claim 10 wherein said recess has walls that hold said bead captive within said recess as said passer pulls said cable behind the bone.

12. A system for passing a surgical cable around a portion of the spine, said the surgical cable comprising a main cable with a thinner, more flexible lead cable with integrally-attached bead affixed to a free end of the lead cable, a low-profile passing tool that receives the bead on the lead cable after the passing tool has been passed around a bone, said passing tool pulling said lead cable along with said main cable under said bone as the passer is withdrawn, said main cable having a preattached fastener having a bore therethrough that accepts the bead on the lead cable and a portion of said main cable, said fastener being crimpable by a surgeon using a suitable crimping tool thereby to lock the main cable to the fastener with the main cable banded about the bone and with a desired level of tension therein.

13. A surgical cable system including a surgical cable and a passer for passing the cable around a bone to which the cable is to be secured:

the cable including a main cable having a first end and a second end;

a fastener at one end of the main cable;

a lead cable at a second end of the main cable, and an enlargement at a free end of the lead cable; and said passer including curved probe having a free end, said probe having a recess therein proximate its free end and a slot extending from the recess to the free end of the probe, said recess being sized to accept the enlargement of the lead cable and the slot being sized to receive a portion of the lead cable proximate said enlargement.

14. A method of passing a surgical cable about bone for securely banding said cable about the bone while maintaining a desired level of tension in the cable banded about said bone, said cable having an enlargement affixed to one end thereof and a fastener preattached to the other end of said cable opposite said lead cable, said fastener having a bore for receiving said enlargement and a portion of said cable, said passer having an elongate probe, said probe having a tip and a recess adjacent said tip for receiving said enlargement on said lead cable, said probe having a partial slot therein leading from said recess to the end of said passer probe, said slot receiving at least a portion of said cable proximate said enlargement when the latter is received within said recess such that at least a portion of said cable is generally in line with the end of said probe, said method comprising the steps of:

inserting the probe of said passer behind the bone without the cable assembly attached to the probe such that the end of the probe is accessible on the other side of the bone to be banded;

inserting said enlargement into said recess with a portion of said cable proximate said enlargement being received within said slot;

withdrawing said passer probe from behind said bone such that said cable is pulled behind said passer probe such that said cable is substantially in line with said passer probe as the latter is withdrawn from behind the bone so that at least a portion of said cable is disposed behind said bone;

disconnecting said cable from said passer probe by removing said enlargement from said recess;

inserting said cable into a bore within said preattached fastener and pulling said cable through said fastener;

applying a desired level of tension to said cable; and while maintaining said desired level of tension on said cable as the latter is banded about said bone, effecting the locking of said fastener to said cable thereby to maintain said main cable banded about said bone with said desired level of tension.

15. The method of claim 14 wherein said fastener is a crimp, and wherein said step of effecting locking of said fastener to said cable comprises crimping said fastener onto the portion of said cable inserted through the fastener such that at least a portion of the fastener securely engages the cable.

16. The method of claim 15 further comprising cutting said cable substantially flush with said crimp.

17. The method of claim 14 wherein said cable has a main cable portion and a more flexible lead cable secured to one end of said main cable, said lead cable carrying said enlargement.

18. A surgical cable assembly comprising:

a multi-stranded flexible main cable having a first end and a second end;

a multi-stranded flexible lead cable attached to said multi-stranded flexible main cable first end, said multi-stranded flexible lead cable having a first end, a free end, and an enlargement on its free end, said multi-stranded flexible lead cable being of a smaller diameter than said multi-stranded flexible main cable, the multi-stranded flexible lead cable being integrally attached to the multi-stranded flexible main cable and having a tapered transition between the smaller diameter multi-stranded flexible lead cable and the larger diameter multi-stranded flexible main cable such as to blend with the diameter of the multi-stranded flexible main cable.

19. The surgical cable assembly of claim 18 further including a preattached fastener that can attach to the surgical cable after appropriate positioning and tensioning.

20. The surgical cable of claim 19 in which the preattached fastener is a crimpable metal tube that is swaged onto the multi-stranded flexible main cable second end, and has an opening therethrough for receiving said multi-stranded flexible lead cable and at least a portion of said multi-stranded flexible main cable, said tube in the region of said opening being mechanically deformable so as to crimp the multi-stranded flexible main cable with respect to the tube thereby to fasten the multi-stranded flexible main cable to the fastener.

* * * * *